United States Patent
Jackson et al.

(10) Patent No.: US 10,585,077 B2
(45) Date of Patent: Mar. 10, 2020

(54) COOLING LIQUID ELUENT OF A CARBON DIOXIDE CHROMATOGRAPHY SYSTEM AFTER GAS-LIQUID SEPARATION

(71) Applicant: Waters Technologies Corporation, Milford, MA (US)

(72) Inventors: Michael R. Jackson, Woonsocket, RI (US); Christopher Seith, Franklin, MA (US); Senthil Bala, Westborough, MA (US); Colin Fredette, Ashland, MA (US)

(73) Assignee: Waters Technologies Corporation, Milford, MA (US)

( * ) Notice: Subject to any disclaimer, the term of this patent is extended or adjusted under 35 U.S.C. 154(b) by 325 days.

(21) Appl. No.: 15/565,347

(22) PCT Filed: Apr. 7, 2016

(86) PCT No.: PCT/US2016/026383
§ 371 (c)(1),
(2) Date: Oct. 9, 2017

(87) PCT Pub. No.: WO2016/164542
PCT Pub. Date: Oct. 13, 2016

(65) Prior Publication Data
US 2018/0106770 A1    Apr. 19, 2018

Related U.S. Application Data

(60) Provisional application No. 62/145,847, filed on Apr. 10, 2015.

(51) Int. Cl.
*B01D 53/02*    (2006.01)
*G01N 30/84*    (2006.01)
(Continued)

(52) U.S. Cl.
CPC .............. *G01N 30/84* (2013.01); *B01D 15/24* (2013.01); *G01N 30/30* (2013.01); *G01N 30/32* (2013.01);
(Continued)

(58) Field of Classification Search
CPC ........ B01D 15/24; B01D 15/40; G01N 30/30; G01N 30/32; G01N 30/62; G01N 30/80; G01N 30/82; G01N 30/84
See application file for complete search history.

(56) References Cited

U.S. PATENT DOCUMENTS 3,290,789 A    12/1966 Zahn et al.
3,374,607 A    3/1968 Fisher et al.
(Continued)

FOREIGN PATENT DOCUMENTS

JP    2007120972 A    5/2007

OTHER PUBLICATIONS

International Search Report and Written Opinion for International Patent Application No. PCT/US2016/026383 dated Jun. 11, 2016 and dated Jul. 11, 2016.

*Primary Examiner* — Christopher P Jones
(74) *Attorney, Agent, or Firm* — Womble Bond Dickinson (US) LLP; Deborah M. Vernon; Heath T. Misley (57) ABSTRACT

The present disclosure relates to methodologies, systems and apparatus for cooling a supersaturated or mixed-phase solution to increase the solubility of gases dissolved therein. In a fluid chromatography system, the mobile phase may include a pressurized mixture including a gas, such as $CO_2$, and prior to fraction collection and/or detection a portion of the gas is extracted via a gas/liquid separator. Cooling the substantially liquid phase eluent exiting the gas/liquid separator increases the solubility of any remnant gas still dissolved within the eluent. The increased solubility of the
(Continued)

remnant gas prevents out gassing, provides more consistent flow of the eluent through the system, and results in more efficient collection and analysis of a desired sample.

21 Claims, 6 Drawing Sheets

(51) Int. Cl.
  *G01N 30/32*  (2006.01)
  *B01D 15/24*  (2006.01)
  *G01N 30/30*  (2006.01)
  *G01N 30/62*  (2006.01)
  *G01N 30/80*  (2006.01)
  *B01D 15/40*  (2006.01)
  *G01N 30/82*  (2006.01)

(52) U.S. Cl.
  CPC ............ *G01N 30/62* (2013.01); *G01N 30/80* (2013.01); *B01D 15/40* (2013.01); *G01N 30/82* (2013.01)

(56) References Cited

U.S. PATENT DOCUMENTS

| | | | |
|---|---|---|---|
| 3,581,465 A | | 6/1971 | Haruki et al. |
| 3,904,483 A | * | 9/1975 | Kurihara .................. C10G 1/02 196/116 |
| 6,358,414 B1 | | 3/2002 | Maiefski |
| 2003/0018213 A1 | * | 1/2003 | Thiebaut ................. C07C 51/12 562/550 |
| 2004/0202573 A1 | * | 10/2004 | van den Brink ..... B01J 19/0046 506/38 |
| 2005/0051468 A1 | | 3/2005 | Miyauchi et al. |
| 2008/0010956 A1 | | 1/2008 | Fogelman et al. |
| 2008/0314812 A1 | | 12/2008 | Kareh et al. |
| 2010/0077874 A1 | * | 4/2010 | Kanomata .......... B01D 11/0203 73/863.21 |
| 2011/0172477 A1 | * | 7/2011 | Sekiguchi ................ B01J 29/40 585/400 |
| 2013/0334117 A1 | | 12/2013 | Joudrey et al. |
| 2014/0283688 A1 | | 9/2014 | Fogelman et al. |
| 2015/0276307 A1 | * | 10/2015 | Ohart ..................... F25J 1/0037 62/613 |
| 2017/0115068 A1 | * | 4/2017 | Gilbert ................. B01D 53/002 |
| 2017/0276654 A1 | * | 9/2017 | Goto .................. B01D 19/0042 |

* cited by examiner

COOLING LIQUID ELUENT OF A CARBON DIOXIDE CHROMATOGRAPHY SYSTEM AFTER GAS-LIQUID SEPARATION

RELATED APPLICATIONS

This application is a National Stage Application of International Application No. PCT/US2016/026383 filed Apr. 7, 2016, which claims priority to U.S. Provisional Patent Application Ser. No. 62/145,847 entitled "Cooling Liquid Eluent of a Carbon Dioxide Based Chromatography System after Gas-Liquid Separation," filed on Apr. 10, 2015, the content of each of which is hereby incorporated by reference in its entirety.

TECHNICAL FIELD

The present disclosure relates to techniques for cooling a supersaturated solution to prevent out gassing from the solution. The present disclosure also relates to methodologies, systems and apparatus for cooling a supersaturated solution in a mixed fluid system, in particular for cooling a supersaturated solution used in $CO_2$-based chromatography systems.

BACKGROUND OF THE TECHNOLOGY

In general, chromatography involves the flowing of a mobile phase over a stationary phase to effect separation. To speed-up and enhance the efficiency of the separation, pressurized mobile phases were introduced. The development of chromatography systems capable of accommodating increasing pressure levels presents a number of non trivial challenges. Carbon dioxide based chromatographic systems use $CO_2$ as a component of the mobile phase flow stream. In some systems, the $CO_2$ based mobile phase is delivered from one or more pumps and carried through the separation column as a pressurized liquid. After exiting the separation column, the mobile phase and the analyte(s) of interest are directed to a detector for analysis or a fraction collector for fraction collection, depending on whether the system is analytical or preparative. This change or fluctuation in density elevates compressibility issues, frustrating typical compressibility compensation schemes. Another challenge is collection and separation of the $CO_2$ media from a sample. Due to the high pressures used in the chromatography column, handling of the separated sample within the $CO_2$ mobile phase is difficult due to phase changes and potential aerosolization of the sample in $CO_2$. An additional challenge is noise interference at a detector. Bubble formation or out gassing of the $CO_2$ can result in noise generation in the detector, which may interfere with sample detection and/or fraction collection.

BRIEF SUMMARY OF THE TECHNOLOGY

Exemplary embodiments of the present technology are directed to chilling a liquid eluent to increase the solubility of a dissolved gas. Further, the embodiments are related to methodologies, systems and apparatus for chilling a supersaturated solution in a mixed fluid system. In particular, the embodiments are related to fluid cooling systems for cooling a supersaturated solution in a $CO_2$ based chromatography system, i.e., a chromatography system in which the mobile phase includes $CO_2$. In a $CO_2$-based chromatography system, the gas and liquid phase portions are separated using, for example, a gas/liquid separator. However, some of the gas remains dissolved in the liquid and can cause problems due to subsequent out gassing. Cooling the substantially liquid phase portion exiting the gas/liquid separator increases the solubility of the dissolved gas and provides more consistent flow of a solution through a given system and more efficient collection and analysis of the solution.

In one aspect, the present technology relates to a fluid chilling system. The system includes: a gas/liquid separator adapted to separate a mixed-phase fluid into a substantially gas phase portion and a substantially liquid phase portion; and a fluid chiller fluidly coupled to the gas-liquid separator and adapted to chill the substantially liquid phase portion to increase the solubility of remnant gases within the substantially liquid phase portion. In one embodiment, the fraction collector is fluidly coupled to the fluid chiller. In another embodiment, the fluid chiller is fluidly coupled to a detector.

Embodiments of this aspect of the technology can include one or more of the following features. In some embodiments, the fluid chiller is adapted to cool the substantially liquid phase portion to a temperature less than an exit temperature of the substantially liquid phase portion from the gas-liquid separator. In some embodiments, the fluid chiller is a vapor compression chiller. In some embodiments, the gas-liquid separator is the gas-liquid separator of a $CO_2$-based chromatography system. In certain embodiments, the gas/liquid separator is a gas/liquid separator of a supercritical fluid chromatography system. In some embodiments, the gas-liquid separator is the gas-liquid separator of a preparative chromatography system. In some embodiments, the gas-liquid separator is the gas-liquid separator of an analytical chromatography system. In some embodiments, the system further includes a fraction valve adapted to dispose of waste contained within the substantially liquid phase portion. In some embodiments, the system further includes a detector configured to detect the presence of gas in the substantially liquid phase portion. In some such embodiments, the gas detector is a UV gas detector. In some embodiments, the detector is in communication with a feedback control unit configured to control a temperature of the fluid chiller based upon detector data.

According to another aspect, the present technology relates to a method of cooling a liquid eluent in a separator process. The method includes flowing a mixed-phase fluid through a gas-liquid separator to create a liquid eluent, flowing the liquid eluent from the gas-liquid separator to a chiller apparatus, and chilling the liquid eluent via the chiller apparatus to increase the solubility of gases present in the liquid eluent. In some embodiments, the chiller apparatus is adapted to chill the liquid eluent prior to fraction collection.

Embodiments of the above aspect can include one or more of the following features. In some embodiments, the liquid eluent is a product of a $CO_2$-based chromatography system. In other embodiments, the liquid eluent is a product of a supercritical fluid chromatography system. In some embodiments, the gas-liquid separator is a component of an analytical fluid chromatography system. In some embodiments, the liquid eluent is a product of a preparative fluid chromatography system. In some embodiments, chilling the liquid eluent includes flowing the liquid eluent through a liquid cooling chiller. In some embodiments, chilling the liquid eluent includes flowing the liquid eluent through atmospheric conditions. In some embodiments, the temperature of the chiller apparatus is lower than the temperature of the liquid eluent upon leaving the gas-liquid separator. In some embodiments, the method further includes disposing of waste within the liquid eluent via a fraction valve. In some embodiments, the method further includes detecting remnant gas within the liquid eluent via a gas detector operatively coupled to the fraction valve. In some embodiments, the gas detector is a UV gas detector.

In a further aspect, the present technology relates to a method of collecting a liquid fraction. This method includes flowing a mixed-phase fluid through a gas-liquid separator to create a liquid eluent containing remnant $CO_2$ dissolved within the liquid eluent, chilling the liquid eluent via a chiller apparatus to increase the solubility of the remnant $CO_2$ within the liquid eluent, flowing the liquid eluent from the chiller apparatus to a fraction collector, and collecting a purified fraction via the fraction collector.

The present disclosure provides a number of advantages over current methods, systems and apparatus. For instance, providing a fluid chiller downstream of a gas-liquid separator and upstream of a fraction collector or detector will increase the solubility of remnant gases that remain dissolved in the fluid and prevent out gassing. Prevention of out gassing provides a more consistent fluid flow through a given system, prevents the formation of bubbles that interfere with detection and allows for more efficient collection of the separated materials.

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION OF THE TECHNOLOGY

Provided herein are methodologies, systems, and apparatus for chilling a supersaturated solution in a fluid chromatography system to increase the solubility of gases dissolved in the fluid. $CO_2$-based chromatography systems differ from other forms of chromatography in that the mobile phase includes $CO_2$. In general, the $CO_2$ or $CO_2$ mixture is used in a supercritical or near supercritical fluid state. To keep the $CO_2$ or $CO_2$ mixture (e.g. $CO_2$ mixed with a solvent such as methanol) at suitable temperature and pressure levels, the entire chromatography system is subjected to a predefined pressure. Dissolved gases in the mobile phase may cause out gassing, the formation of bubbles, or otherwise interfere with subsequent flow and downstream processes, such as fraction collection and detection. Therefore, the mobile phase gas is removed from the supersaturated mixed-phase solution in a gas/liquid separator before fraction collection and/or sample analysis. However, because this separation takes place under high pressure, the liquid eluent may still include significant amounts of dissolved gas even after exiting a gas/liquid separator. This dissolved gas can come out of the solution when the pressure on the liquid drops, which can result in the formation of bubbles or cause the flow of the liquid after the gas/liquid separator to be inconsistent. This inconsistent flow and bubble formation interferes with subsequent processing, such as fraction collection and detection. To prevent the gas from coming out of the solution, a chiller is placed on the liquid stream after the gas/liquid separator to increase the solubility of the dissolved gases, which helps prevent the dissolved gases from coming out of the solution as the pressure drops. As provided herein, the supersaturated liquid eluent is chilled to increase the solubility of remnant gas dissolved in the solution and minimize or eliminate the deleterious effects of carbon dioxide expansion on the solvent, the analyte(s) of interest, the separation, the detection of the analyte(s) of interest, and other related aspects in a $CO_2$-based chromatography system. Prevention of out gassing enhances fraction collection performance and/or detection accuracy.

In some embodiments, a $CO_2$-based chromatography system employs $CO_2$ pumps and back pressure regulators in order to regulate the temperature and pressure levels of the system and maintain the solution in a supercritical fluid state or near supercritical state. In one embodiment, a primary automatic back pressure regulator and a secondary automatic back pressure regulator are separated by a heater and work together to manage the pressure within the $CO_2$-based chromatography system upstream of the gas/liquid separator. Such back pressure regulators are typically employed downstream of the chromatography column to maintain a predefined pressure. After passing a mobile phase through a column to effect separation, decompression and removal of a portion of the mobile phase gas from the mixed-phase eluent may be accomplished in various ways. In one embodiment, the mixed-phase fluid or eluent is passed through a gas/liquid separator in order to remove a majority of the dissolved gas prior to sample analysis or fraction collection. In other embodiments, a degasser apparatus may be used, alone or in connection with a gas/liquid separator, to separate the dissolved gas from the solution. After separation of the gas via the gas/liquid separator and/or degasser, the extracted gas may be disposed of or recompressed and recycled within the system. $CO_2$ is more environmentally friendly and easier to recycle and/or dispose of than other mobile phase gases, and therefore, in some embodiments the primary mobile phase gas is $CO_2$. Other solvent gases and/or co-solvents may include, for example, methanol, ethanol, isopropyl alcohol, acetonitrile, chloroform, or ethyl acetate.

After a portion of the mobile phase gas has been extracted from the mixed-phase eluent, the substantially liquid phase portion of the eluent may still have significant amounts of gas, such as $CO_2$, dissolved within it because of the pressures of the fluid flowing from the gas/liquid separator. In some embodiments, the fluid exiting the gas/liquid separator may be pressurized in the range of 30-50 psi. Exposure of a liquid mixture containing dissolved $CO_2$ to atmospheric pressure results in a sudden expansion of the liquid mixture, forming an aerosol. This out gassing can cause bubble formation, interfere with the flow rate of the fluid, or decrease the amount of a sample that may be collected from a fraction collection vessel.

To ensure that any remnant $CO_2$ dissolved within the substantially liquid phase eluent does not interfere with fraction collection, sample detection, or other downstream processes, methods may be implemented to maintain the $CO_2$ substantially dissolved within the eluent. One such method includes the use of chillers and feedback controls that can chill the substantially liquid phase eluent, thus increasing the solubility of any remnant $CO_2$. In some embodiments, a detector may be used to detect the presence of $CO_2$ bubbles within the eluent, and the detector may be in communication with a feedback control unit that controls the temperature of the chiller based on whether $CO_2$ is detected in the eluent. Increasing the solubility of $CO_2$ within the eluent provides more accurate sample detection in analytical chromatography systems. Similarly, in preparative chromatography systems the increased solubility prevents loss of the fraction sample that may be caused by out gassing or aerosolization.

In some embodiments, a chiller may employ vapor compression techniques, absorption refrigeration, or free cooling techniques. For example, Peltier-based or other thermoelectric cooling devices may be implemented. More generally, the chiller may be any cooling system that exposes the eluent, directly or indirectly, to a temperature less than the temperature of the gas/liquid separator. In some embodiments, the chiller exposes the eluent to a temperature less than the temperature of the eluent when it exits the gas/liquid separator. In one particular embodiment, the chiller may be a counter-current heat exchanger using a cooling fluid or a cooling block chilled using a thermoelectric cooling device. The target temperature for the eluent may vary, in some embodiments, based on the mobile phase gas being used, the sample being prepared and/or analyzed, or based on data from a detector.

In some embodiments, a gas or bubble detector, such as a UV detector or a refractive index (RI) detector, may be used to detect bubbles or gas within the eluent or to determine when the peak of interest elutes. The detector may be used to control the fraction valve of the fraction collector in order to retrieve the fraction, in some embodiments. In other embodiments, a detector may be used to detect bubbles within the eluent and may include a feedback loop to control the temperature of the chiller, thus reducing subsequent out-gassing or bubble formation. Such detectors may be positioned before or after the gas/liquid separator, in exemplary $CO_2$-based chromatography systems.

Figure 1:
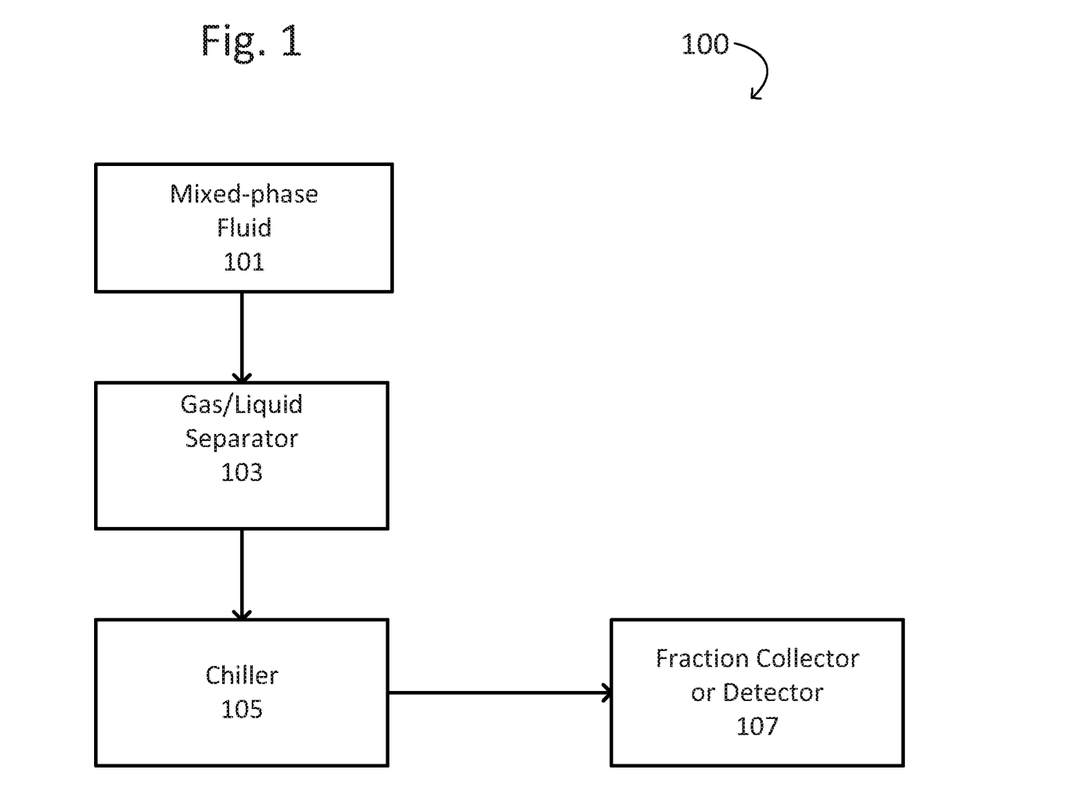
FIG. 1 is a block diagram of an exemplary fluid chilling system, according to one embodiment of the present disclosure.

FIG. 1 depicts a block diagram of an exemplary fluid chilling system 100, according to one embodiment of the present disclosure. The fluid chilling system 100 comprises a mixed-phase or supersaturated fluid 101, a gas/liquid separator 103, a fluid chiller 105, and a fraction collector or detector 107. In some embodiments, the fluid chilling system 100 is part of a SFC system, such as a $CO_2$-based chromatography system. In this particular embodiment, the mixed-phase fluid 101 is conducted to the gas/liquid separator 103 which separates the mixed-phase fluid into a substantially gas phase portion and a substantially liquid phase portion. The substantially gas phase portion (e.g. $CO_2$) that was extracted via the gas/liquid separator 103 may be disposed of or recompressed and recycled within the system, in some embodiments. The gas/liquid separator 103 is fluidly coupled to a fluid chiller 105, which receives the substantially liquid phase eluent from the gas/liquid separator 103 and chills the eluent. As described above, various types of chillers may be used to cool the substantially liquid phase eluent to a temperature less than the exit temperature of the eluent exiting the gas/liquid separator.

The chiller 105 may include, in some embodiments, one or more refrigeration compressors which compress the refrigerant to a relatively high temperature and pressure. Suitable types of refrigeration compressors may include, for example, reciprocating compressors, scroll compressors, screw compressors, or centrifugal compressors. Once the refrigerant has been compressed, it is sent to a condenser where the refrigerant releases heat and condenses to a liquid form. This liquid refrigerant may then be sent to an expansion or metering device which (flash evaporation) to create a fluid-gas refrigerant mixture that is cooler than the temperature of the gas/liquid separator, or alternatively, cooler than the temperature of the substantially liquid phase eluent. This fluid-gas refrigerant mixture is then sent to an evaporator where it may interact with and cool the substantially liquid phase eluent.

As discussed above, chilling the substantially liquid phase eluent will increase the solubility of any remnant gases that are dissolved therein. In the embodiment shown in FIG. 1, an outlet of the fluid chiller 105 is fluidly coupled to a fraction collector and/or detector 107, which collects a fraction sample or performs analysis on the eluent. In a preparative liquid chromatography system, the chilled eluent is directed to a fraction collector, which may be controlled by a detector that detects when to collect the fraction, whereas in an analytical liquid chromatography system the chilled eluent may be only directed to a detector. In some embodiments, detection and analysis may be performed using, for example, a bubble detector, UV/Vis detector, RI detector, mass spectrometry, flame ionization detection (FID), evaporative light scattering, or other suitable chromatography detection techniques.

Figure 2:
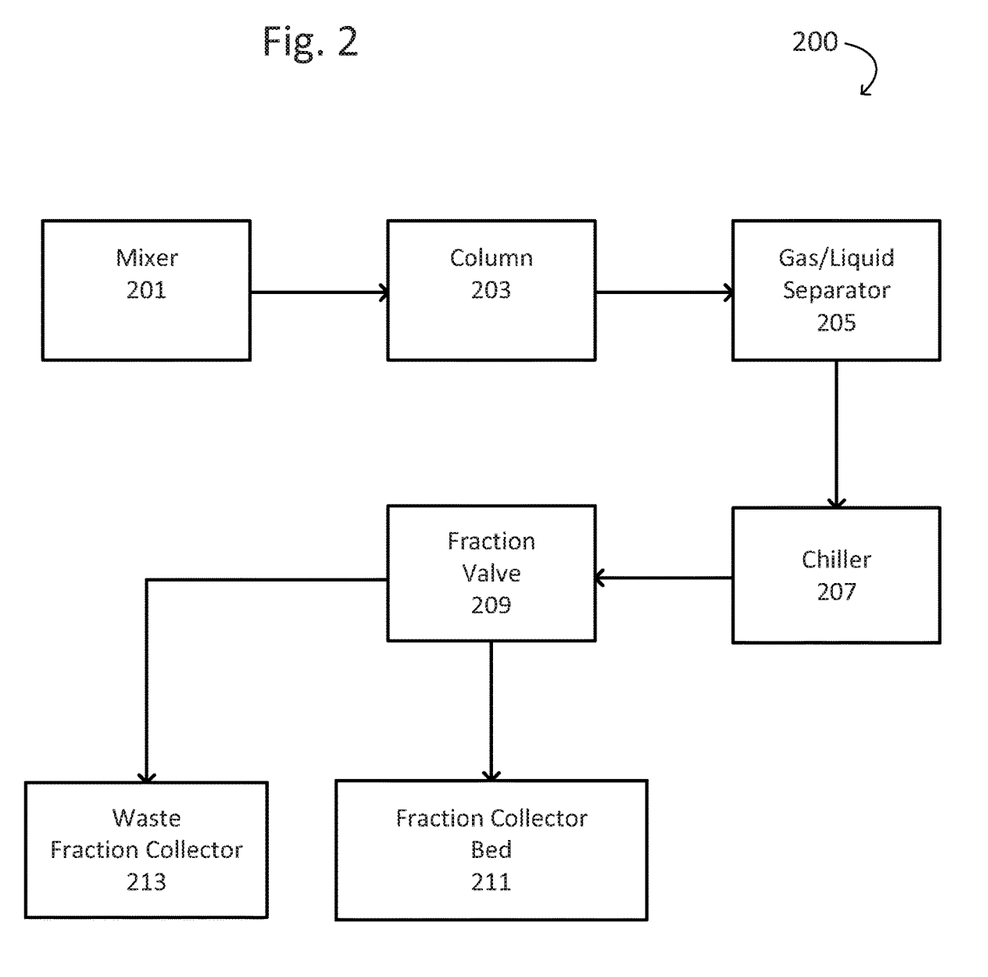
FIG. 2 depicts a block diagram of an exemplary fluid chromatography system including a fluid chilling system as described in FIG. 1, configured according to one embodiment of the present disclosure.

FIG. 2 depicts a block diagram of an exemplary $CO_2$-based chromatography system 200 including a fluid chilling system such as the one described in FIG. 1. The $CO_2$-based chromatography system 200 comprises a mixer 201, a column 203, a gas/liquid separator 205, a fluid chiller 207, a fraction valve 209, a fraction collector bed 211, and a waste fraction collector 213. In this particular embodiment, the $CO_2$-based chromatography system 200 is a preparative system configured to prepare and collect a fraction in the fraction collector bed 211. In some embodiments, a pressurized mixed-phase fluid (i.e., having more than one state of fluid) is conducted from an outlet of the mixer 201 to the column 203. After exiting the column 203, the eluent is conducted to the gas/liquid separator 205, which extracts a majority of the dissolved mobile phase gas. A substantially liquid phase portion of the mixed-phase eluent is then conducted from an outlet of the gas/liquid separator 205 to the chiller 207, which cools/chills the substantially liquid phase portion of the mixed-phase fluid to increase the solubility of remnant gases within the fluid. After chilling the substantially liquid phase eluent, the eluent is conducted to a fraction valve 209, which can direct the desired fraction to a fraction collector bed 211 and direct any waste to a waste fraction collector 213.

In one particular example, the preparative fluid chromatography system 200 is a $CO_2$-based chromatography system used to prepare a fraction of warfarin. In such an embodiment, the mobile phase may include $CO_2$ or a $CO_2$ mixture (e.g. $CO_2$ mixed with a co-solvent such as methanol). After the mobile phase is passed through a column 203, the eluent is conducted to a gas/liquid separator 205 to extract a portion of the dissolved $CO_2$. Even after the gas/liquid separator 205 has extracted a majority of the $CO_2$, a significant amount of $CO_2$ may still remain dissolved in the mobile phase because of the higher pressure required to use $CO_2$ or a $CO_2$ mixture as the mobile phase. The fraction valve 209 is configured to collect the purified fraction via the fraction collector bed 211.

Figure 3:
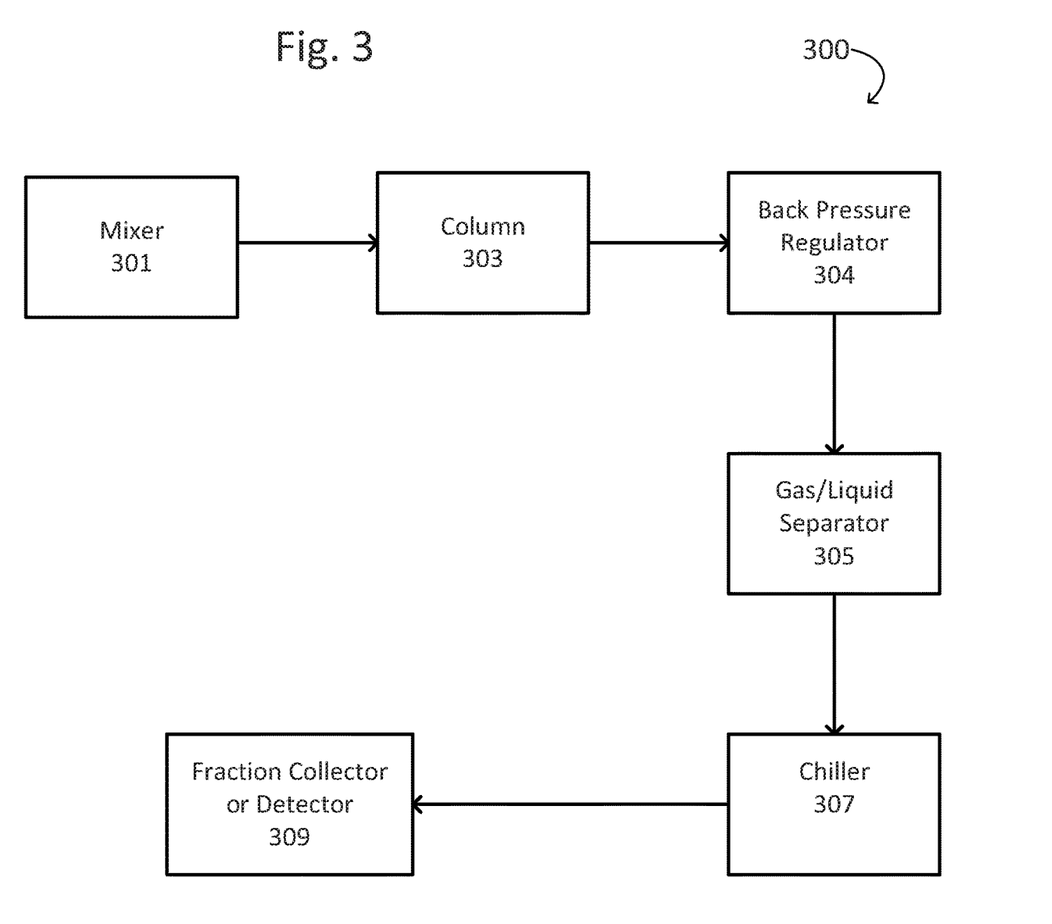
FIG. 3 depicts a block diagram of an exemplary fluid chromatography system including a fluid chilling system as described in FIG. 1, configured according to one embodiment of the present disclosure.

FIG. 3 depicts a block diagram of an exemplary fluid chromatography system 300 including a fluid chilling system as described in FIG. 1, configured according to one embodiment of the present disclosure. The $CO_2$-based chromatography system 300 comprises a mixer 301, a column 303, a back pressure regulator 304, a gas/liquid separator 305, a fluid chiller 307, and a fraction collector or detector 309. In this particular embodiment, the back pressure regulator 304 is positioned downstream of the chromatography column 303 to maintain the predefined pressure required to keep the mixed-phase fluid at suitable temperature and pressure levels. The chiller 307 is applied to the gas/liquid separator 305 or at least to the liquid separation portion outlet to increase the solubility of $CO_2$ or other gases therein. As a result, $CO_2$ does not outgas or substantially outgas from the liquid eluent as an aerosol when exiting the highly pressurized system.

Figure 4:
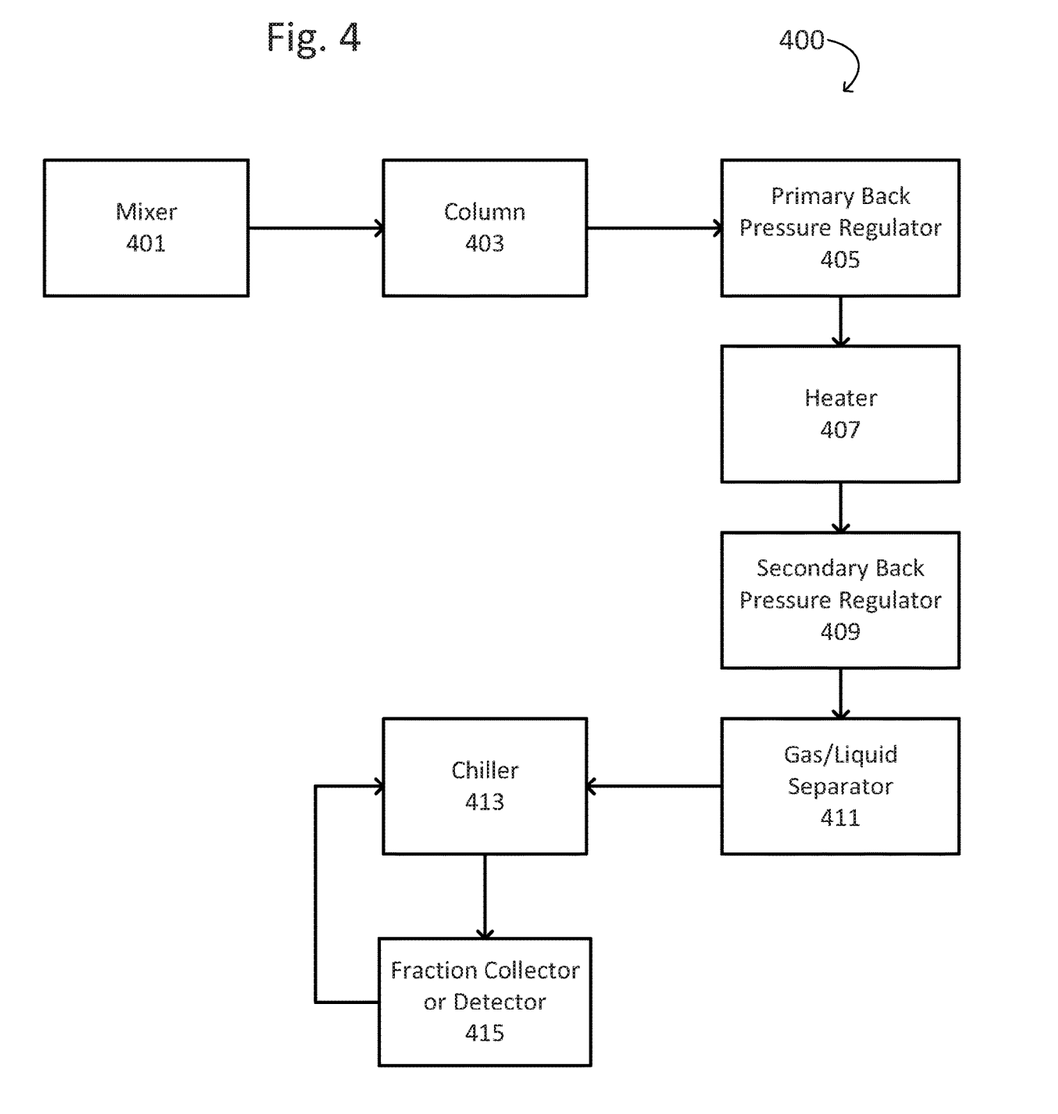
FIG. 4 depicts a block diagram of an exemplary fluid chromatography system including a fluid chilling system as described in FIG. 1, configured according to another embodiment of the present disclosure.

FIG. 4 depicts a block diagram of an exemplary fluid chromatography system 400 including a fluid chilling system as described in FIG. 1, configured according to another embodiment of the present disclosure. The fluid chromatography system 400 comprises a mixer 401, a column 403, a primary back pressure regulator 405, a heater 407 disposed downstream of the primary back pressure regulator 405 and upstream of a secondary back pressure regulator 409, a gas/liquid separator 411, a fluid chiller 413, and a fraction collector and/or detector 415. Similar to the system described in reference to FIG. 3, the fluid chromatography system 400 employs backpressure regulators 405 and 409, separated by heater 407, to regulate the pressure and temperature levels of the mixed-phase fluid and maintain the fluid at suitable temperature and pressure levels. The fluid chiller 413 cools the mixed-phase fluid in order to increase the solubility any remnant gas dissolved within the fluid and prevent aerosolization or out gassing. In preparative chromatography systems, out gassing may decrease the amount of sample collected because portions of the sample are lost along with the gas because the aerosolized liquid carries some of the sample with it. In analytical chromatography systems, out gassing and bubble formation within a sample interferes with sample detection. As a result, aspects and features of the present disclosure teach cooling the mixed-phase fluid to increase the solubility of the mobile phase gas.

As discussed above, in analytical systems a gas detector 415 may be used for sample detection, as well as to detect bubbles present within the sample. If bubbles are present within the sample, the detector 415 can be connected to the chiller 413 via a feedback loop in order to control the temperature of the chiller. In one such embodiment, if the detector 415 detects bubbles within the sample, it may reduce the chiller temperature in order to further increase the solubility of any dissolved gases and prevent further bubble formation. In preparative systems, the chilled eluent is directed from the chiller 413 to a fraction collector 415. In some embodiments, the fraction collector 415 may include or be controlled by a detector which detects when to collect the fraction and controls the fraction valve of the fraction collector. The detector may also be used to detect bubble formation in the sample or fraction and may control the temperature of the chiller to prevent further bubble formation and/or out-gassing. In some embodiments, a detector may be positioned before or after the gas/liquid separator in order to monitor the temperature of the chiller based on bubble formation within the eluent.

Figure 5:
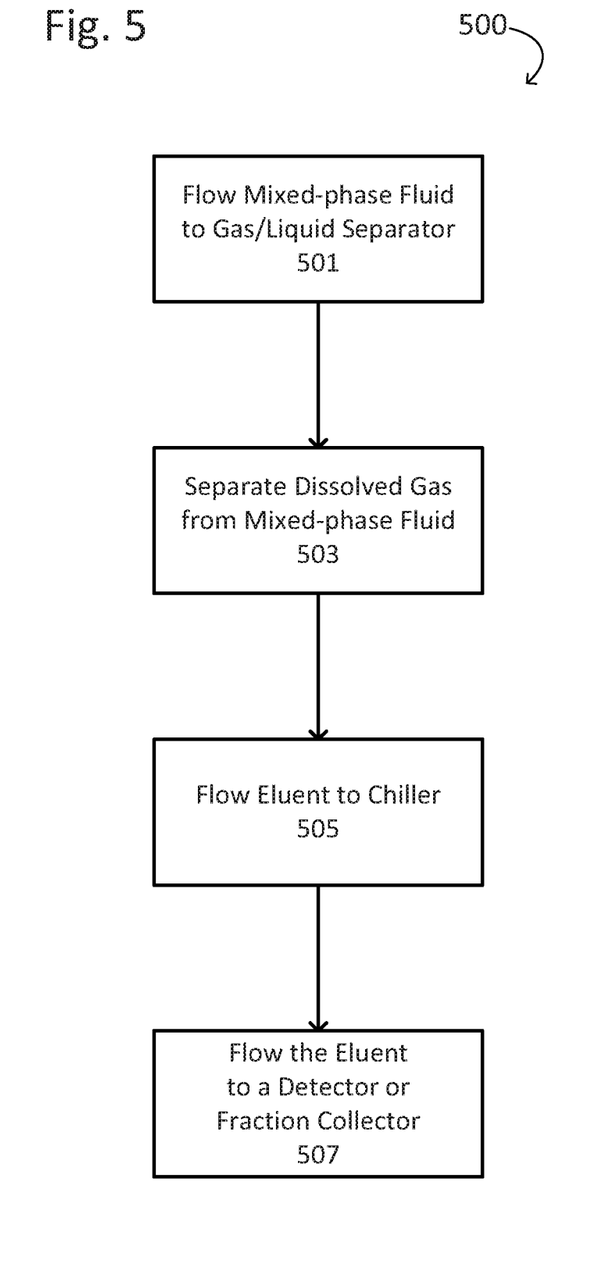
FIG. 5 is a flow chart of an exemplary method for chilling a mixed-phase fluid, according to one embodiment of the present disclosure.

FIG. 5 is a flow chart of an exemplary method 500 for chilling a mixed-phase fluid, according to one embodiment of the present disclosure. In this particular embodiment, the method begins with flowing 501 a mixed-phase fluid to a gas/liquid separator. In some embodiments, the mixed-phase fluid is the product of a $CO_2$-based chromatography system operated under supercritical fluid conditions. The method continues with separating 503 the dissolved mobile phase gas from the mixed-phase fluid via the gas/liquid separator. As described above, although a gas/liquid separator may extract a majority of the gas from the mixed-phase fluid, a portion of gas may still remain dissolved in the substantially liquid phase portion. The method continues with chilling 505 the substantially liquid phase fluid in order to increase the solubility of any remnant gases present in the substantially liquid phase portion. The substantially liquid phase fluid may be chilled via a chiller, as described above, which may include any apparatus for decreasing the temperature of the fluid leaving the gas/liquid separator. In some embodiments, chilling 505 the substantially liquid phase fluid may be accomplished via vapor compression, absorption refrigeration, or free cooling techniques. The method may continue with flowing 507 the chilled fluid to a fraction collector or detector. In a preparative fluid chromatography system the chilled fluid is flowed to a fraction collector, whereas in an analytical fluid chromatography system the chilled fluid is flowed to a detector. In preparative chromatography systems, out gassing may decrease the amount of sample collected because portions of the sample are lost along with the gas. In analytical chromatography systems, out gassing interferes with sample detection and analysis by causing bubbles within the sample. As a result, aspects and features of the present disclosure teach chilling 505 the mixed-phase fluid to increase the solubility of any remnant gas dissolved within the fluid and prevent aerosolization or out gassing.

Figure 6:
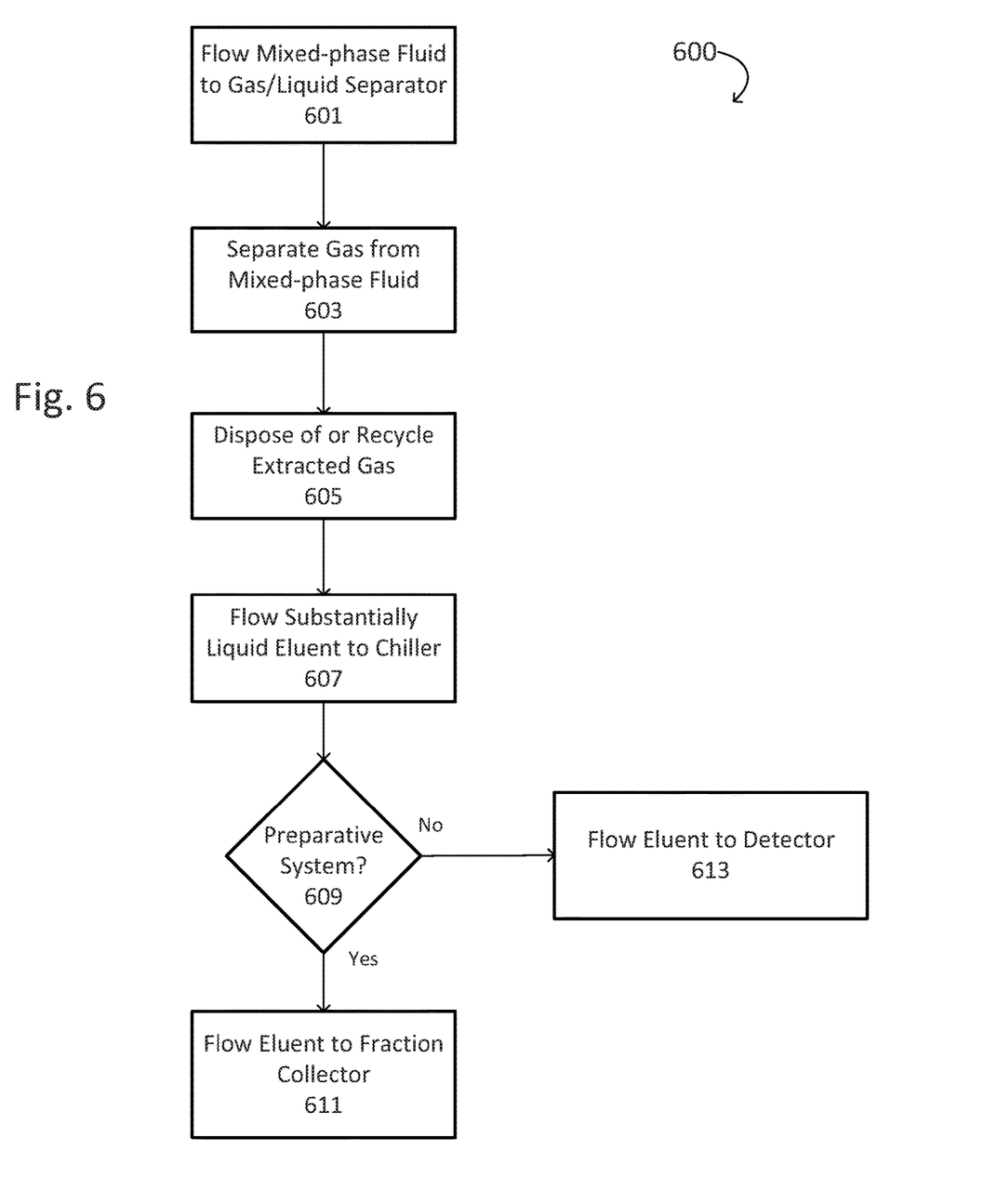
FIG. 6 is a flow chart illustrating exemplary methods for chilling a mixed-phase fluid, according to embodiments of the present disclosure.

FIG. 6 is a flow chart illustrating exemplary methods 600 for collecting or analyzing a liquid fraction, according to embodiments of the present disclosure. In this particular embodiment, the method begins with flowing 601 a mixed-phase fluid to a gas/liquid separator. As discussed above, the mixed-phase fluid may be the product of a $CO_2$-based chromatography system in which the mobile phase is a pressurized mixture including $CO_2$. The method continues with separating 603 at least a portion of the gas from the mixed-phase fluid. After the gas/liquid separator has separated the mixed-phase fluid into a gas phase portion and a substantially liquid phase portion, the extracted gas may be disposed of or recycled 605. In some embodiments, the gas extracted by the gas/liquid separator is primarily $CO_2$, which is more environmentally friendly and more easily disposed of than other mobile phase gases. The method continues with flowing 607 the substantially liquid phase eluent (e.g., some dissolved $CO_2$ gas may still be dissolved within the liquid phase) from an outlet of the gas/liquid separator to a chiller, resulting in a cooled liquid eluent. As discussed above, several different types of chillers may be implemented, according to various embodiments of the disclosure, and the target temperature for the cooled eluent may vary depending on the mobile phase gas being used and/or the sample being prepared or analyzed. In some embodiments, the target temperature of the chiller is controlled using feedback from a gas detector, which can detect bubbles within the sample and adjust the temperature accordingly. After the eluent is chilled, the method may continue with determining 609 whether the eluent is to be sent to a fraction collector as part of a preparative fluid chromatography system or whether the eluent is to be sent only to a detector as part of an analytical fluid chromatography system. If the system is a preparative chromatography system, the method continues with flowing 611 the eluent to a fraction collector. In some embodiments, the fraction valve of the fraction collector is controlled by a detector that can detect when the peak elutes. If, however, the system is an analytical chromatography system, the method continues with flowing 613 the eluent to a detector, such as a UV detector. As discussed above, out gassing may decrease the amount of sample collected in a preparative chromatography system because portions of the sample may be lost in the aerosol, while bubble formation within the eluent or sample can interfere with sample detection. Thus, chilling the eluent to increase the solubility of any remnant gas dissolved within the eluent can prevent bubble formation, and outgassing or aerosolization.

In alternative embodiments, the techniques described above with respect to $CO_2$-based chromatography systems may be applicable to other types of mobile phases and applied to systems that suffer from the problems of bubble formation or outgas sing of a mobile phase gas. In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

As used herein, the term "supersaturated solution" means a state of a solution that contains more of a solute than would be present under normal conditions, i.e., atmospheric pressure and ambient temperature. For example, carbonated water is a supersaturated solution of carbon dioxide gas in water. At atmospheric pressure, the carbon dioxide gas escapes very slowly from the supersaturated liquid. However, at the elevated pressure in the bottle, more carbon dioxide can dissolve in water than at atmospheric pressure.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

What is claimed is:

1. A fluid chilling system, comprising:
   a gas-liquid separator adapted to separate a mixed-phase fluid into a substantially gas phase portion and a substantially liquid phase portion;
   a fluid chiller fluidly coupled to the gas-liquid separator and adapted to chill the substantially liquid phase portion to increase the solubility of remnant gases within the substantially liquid phase portion; and
   a fraction collector fluidly coupled to the fluid chiller.

2. The system of claim 1, wherein the fluid chiller is adapted to cool the substantially liquid phase portion to a temperature less than an exit temperature of the substantially liquid phase portion from the gas-liquid separator.

3. The system of claim 2, wherein the fluid chiller is a vapor compression chiller.

4. The system of claim 1, wherein the gas-liquid separator is the gas-liquid separator of a $CO_2$-based chromatography system.

5. The system of claim 1, wherein the gas-liquid separator is the gas-liquid separator of a preparative chromatography system.

6. The system of claim 1, wherein the gas-liquid separator is the gas-liquid separator of an analytical chromatography system.

7. The system of claim 1, further comprising a fraction valve adapted to dispose of waste contained within the substantially liquid phase portion.

8. The system of claim 1, further comprising a detector configured to detect the presence of gas in the substantially liquid phase portion.

9. The system of claim 8, wherein the detector is in communication with a feedback control unit configured to control a temperature of the fluid chiller based upon detector data.

10. The system of claim 8, wherein the gas detector is at least one of a UV gas detector and a refractive index-based gas detector.

11. A method of cooling a liquid eluent in a separator process, comprising:
    flowing a mixed-phase fluid through a gas-liquid separator to create a liquid eluent;
    flowing the liquid eluent from the gas-liquid separator to a chiller apparatus; and
    chilling the liquid eluent via the chiller apparatus to increase the solubility of gases present in the liquid eluent prior to fraction collection.

12. The method of claim 11, wherein the liquid eluent is a product of a $CO_2$-based chromatography system.

13. The method of claim 11, wherein the gas-liquid separator is a component of an analytical fluid chromatography system.

14. The method of claim 11, wherein the liquid eluent is a product of a preparative fluid chromatography system.

15. The method of claim 11, wherein chilling the liquid eluent comprises flowing the liquid eluent through a liquid cooling chiller.

16. The method of claim 11, wherein chilling the liquid eluent comprises flowing the liquid eluent through atmospheric conditions.

17. The method of claim 11, wherein the temperature of the chillier apparatus is lower than the temperature of the liquid eluent upon leaving the gas-liquid separator.

18. The method of claim 11, further comprising disposing of waste within the liquid eluent via a fraction valve.

19. The method of claim 18, further comprising detecting remnant gas within the liquid eluent via a gas detector operatively coupled to the fraction valve.

20. The method of claim 18, wherein the gas detector is a UV gas detector.

21. A method of collecting a liquid fraction, comprising:
    flowing a mixed-phase fluid through a gas-liquid separator to create a liquid eluent containing remnant $CO_2$ dissolved within the liquid eluent;
    chilling the liquid eluent via a chiller apparatus to increase the solubility of the remnant $CO_2$ within the liquid eluent;
    flowing the liquid eluent from the chiller apparatus to a fraction collector; and
    collecting a purified fraction via the fraction collector.

* * * * *